(12) United States Patent
Kirschner et al.

(10) Patent No.: US 6,352,713 B1
(45) Date of Patent: Mar. 5, 2002

(54) NUTRITIONAL COMPOSITION

(75) Inventors: Mitchell I. Kirschner, St. Louis; R. Saul Levinson, Chesterfield; George N. Paradissis, St. Louis, all of MO (US)

(73) Assignee: Drugtech Corporation, Wilmington, DE (US)

( * ) Notice: Subject to any disclaimer, the term of this patent is extended or adjusted under 35 U.S.C. 154(b) by 0 days.

(21) Appl. No.: 09/451,849

(22) Filed: Dec. 1, 1999

(51) Int. Cl.$^7$ .............. A61K 9/28; A61K 9/68; A61K 47/00; A23G 3/30
(52) U.S. Cl. .............. 424/441; 424/439; 424/440; 426/3; 426/73; 426/321
(58) Field of Search ................. 424/441, 439, 424/440; 426/73, 3, 321

(56) References Cited

U.S. PATENT DOCUMENTS

| | | |
|---|---|---|
| 3,125,491 A | 3/1964 | Elowe et al. |
| 3,446,899 A | 5/1969 | Cavelli et al. |
| 4,327,076 A | 4/1982 | Puglia et al. ............... 424/38 |
| 4,327,077 A | 4/1982 | Puglia et al. ............... 424/38 |
| 4,822,816 A | 4/1989 | Markham ................. 514/474 |
| 4,935,243 A | 6/1990 | Borkan et al. .............. 424/441 |
| 4,968,716 A | * 11/1990 | Markham ................. 514/474 |
| 5,002,780 A | 3/1991 | Batka et al. ................ 426/72 |
| 5,070,085 A | 12/1991 | Markham ................. 514/161 |
| 5,215,750 A | 6/1993 | Keane, II .................. 424/440 |
| 5,288,497 A | 2/1994 | Stanley et al. ............. 424/440 |
| 5,312,626 A | 5/1994 | Gergely et al. ............. 424/441 |
| 5,770,217 A | * 6/1998 | Kutilek, III et al. ......... 424/442 |
| 5,869,084 A | * 2/1999 | Paradissis et al. .......... 424/439 |
| 5,965,162 A | 10/1999 | Fuisz et al. ............... 424/464 |

OTHER PUBLICATIONS

Warner Chilcott, advertising brochure for NataChew Prenatal Vitamin Tablet with Iron 1999.*
Physician's Desk Reference, 3212 (53$^{rd}$ Ed. 1999).
Physician's Desk Reference, 3162 (53$^{rd}$ Ed. 1999).
Physician's Desk Reference, 3128 (53$^{rd}$ Ed. 1999).
Physician's Desk Reference, 2917 (53$^{rd}$ Ed. 1999).
Physician's Desk Reference, 2916 (53$^{rd}$ Ed. 1999).
Physician's Desk Reference, 2802 (53$^{rd}$ Ed. 1999).
Physician's Desk Reference, 1692 (53$^{rd}$ Ed. 1999).
Physician's Desk Reference, 1522 (53$^{rd}$ Ed. 1999).
Physician's Desk Reference, 1011 (53$^{rd}$ Ed. 1999).
Warner Chilcott, advertising brochure for NataChew™ Prenatal Vitamin Tablet with Iron, 1999.

* cited by examiner

*Primary Examiner*—Thurman K. Page
*Assistant Examiner*—S. Tran
(74) *Attorney, Agent, or Firm*—Nath & Associates PLLC; Gary M. Nath; Joshua B. Goldberg

(57) ABSTRACT

The present inventive subject matter is directed to novel chewable prenatal nutritional supplements which contain vitamin C, as well as novel methods for providing optimal vitamin C supplementation to pregnant women. The present invention is also directed to novel compositions and methods for providing nutritional supplementation to individuals planning to conceive a child.

51 Claims, No Drawings

NUTRITIONAL COMPOSITION

BACKGROUND OF THE INVENTION

1. Field of the Invention

The present invention is directed to a novel chewable prenatal nutritional supplement which contains vitamin C, and which optionally contains folic acid, minerals, other vitamins and/or additives. The supplement is substantially non-acidic and therefore provides vitamin C in adequate levels for pregnant woman while minimizing or eliminating gastric upset, dyspepsia and/or tooth enamel erosion. The present invention is also directed to an improved method for providing vitamin C supplementation to pregnant women in a manner designed to eliminate or minimize gastric upset, dyspepsia and/or tooth enamel erosion.

2. Description of the Related Art

It is well established that pregnant women have heightened nutritional requirements. A mother's body provides the environment in which development of the embryo and fetus occur. See *Understanding Nutrition*, 479–480 (Whitney and Rolfes Eds. 6th Ed., 1993). Accordingly, the mother's nutritional status during pregnancy directly impacts the development of the fetus and embryo and is therefore implicated with regard to the occurrence of birth defects. See Id. In particular, during the first 20–25 days of pregnancy, the placenta is not yet formed and fetal circulation is not yet established. Therefore, during this period the fetus is nourished via digested maternal uterine cells and the diffusion of blood exudates. See Schorah "Importance of Adequate Folate Nutrition in Embryonic and Early Fetal Development", *Vitamins and Minerals in Pregnancy and Lactation*, 167–176 (Berger, Ed., Vol. 16, 1988). It is believed that a good nutrient supply during the first 20–25 days of pregnancy is necessary to provide optimal concentrations of essential micronutrients to the endometrium. See Id.

Furthermore, increased occurrence of birth defects have been linked to inadequate nutrition in the women. Cases of infants born with a neural tube defect, i.e., spina bifida or anacephaly, have been documented in women with various nutritional deficiencies, primarily low blood folic acid and vitamin C concentrations. Smithells, "Vitamin deficiencies and neural tube defects", *Arch Dis Child*, 51:944–50 (1976).

Vitamin C, also known as ascorbic acid, is an essential aspect of proper nutrition for various reasons, including but not limited to its role as an antioxidant. Many nutritional substances important to the body are destroyed by oxidation, but vitamin C, by becoming oxidized itself, can protect these substances. *Understanding Nutrition*, 294 (Whitney and Rolfes Eds. 6th Ed., 1993). Food manufacturers will often add vitamin C to their products to protect the food from oxidation. Inside the body, vitamin C protects other vitamins and minerals from oxidation. For example, in the intestines, vitamin C protects iron and thus promotes its bioavailability. Id. at 296–8.

Vitamin C also helps form collagen, the fibrous, structural protein that comprises connective tissue. The amino acids hydroxyproline and hydroxylysine facilitate the binding of collagen into a strong, rope-like structure. Id. The enzyme that hydrolyzes proline and lysine requires vitamin C to complete the reaction. When a person is wounded, collagen glues the tissue back together and forms scars. Cells are also held together by collagen. For example, the cells that make up the capillary walls that expand and contract with the beating of the heart are held together by collagen. As a result, vitamin C may play a role in preventing high blood pressure. Id. at 307–9.

Vitamin C is also crucial in the metabolism of several amino acids. Some of these amino acids are converted into the hormones epinephrine and thyroxin. As a result, the adrenal gland contains a higher concentration of vitamin C than any other organ. During emotional and physical stress, the adrenal gland releases vitamin C to assist in the creation of epinephrine and thyroxin. Id.

Exposure to colds and infection increases the need for vitamin C. Thyroxin, made with vitamin C, regulates the metabolic rate, which speeds up whenever the body needs to produce heat—for example during a fever or in very cold weather. Id. at 326.

Different countries set different daily requirements for vitamin C, but most agree that 10 mg each day will present vitamin C deficiency (scurvy). At 60 mg each day, the body will stop responding to further vitamin C intake. At 100 mg each day, all the body's tissue's are saturated, and the body will begin to excrete excess vitamin C. The Recommended Daily Allowance (RDA) of vitamin C in the United States is 60 mg per day. Id. at 327. However, more vitamin C may be indicated if the patient has just gone through some physiological or psychological stress, consumes alcohol daily or smokes. Pregnant or breast-feeding women also require additional vitamin C, due to the portion of their daily intake that goes to the fetus or breast milk. *Current Pediatric Diagnosis and Treatment* (13th Ed. 1997).

Vitamin C deficiency is referred to as scurvy. Because vitamin C is water soluble it is quickly excreted. With an inadequate daily intake of vitamin C, the body's store of vitamin C is depleted at a rate of about 3 percent each day. Two early signs of scurvy are bleeding gums and atherosclerotic plaques. After 5 weeks, degenerating muscles (including the heart), scaly skin and wounds that will not heal appear. Hysteria results, followed by sudden death. Scurvy can be reversed by moderate doses of vitamin C, in the area of 100 mg per day. *Understanding Nutrition*, 328 (Whitney and Rolfes Eds. 6th Ed., 1993)

Too much vitamin C can be toxic, causing cramps, nausea and diarrhea. Too much vitamin C can also obscure the presence of diabetes. Toxic levels can start at 2 g a day. Id.

Good sources of vitamin C include citrus fruits, broccoli, cauliflower, strawberries, potatoes and organ meats such as kidney and liver. Grains and milk, except for breast milk, are devoid of vitamin C. Id. at 330.

Folic acid, also known as pteroylglutamic acid and vitamin $B_9$, plays an important role in cell division, erythropoiesis and protein synthesis, all of which are processes important to growing tissues. Folic acid is part of an enzyme complex that changes vitamin $B_{12}$ into its active form and helps synthesize amino acids into the new DNA required for dividing cells. *Understanding Nutrition*, 311 (Whitney and Rolfes Eds. 6th Ed., 1993)

Folic acid has a low bioavailability, and only about half of all dietary folic acid is available to the body. The RDA of folic acid is 150–200 mcg for adult males, 150–180 mcg for adult females and 400 mcg for pregnant females. *Current Pediatric Diagnosis and Treatment*, (13th Ed. 1997).

Folic acid deficiency can occur when there is a need for increased cell proliferation, such as that experienced during pregnancy. Pregnant women require more folic acid than normal and are at greater risk for folic acid deficiency. Folic acid supplementation during pregnancy is believed to reduce the risk of neural tube defects, such as spina bifida, in infants. Id.

The acidity of gastric juices in the stomach registers at about 2 on the pH scale, and stomach enzymes work best at a pH lower than 2. However, too much acid can cause stomach pain. Stomach Emptying Rates and Drug Absorption, www.medscape.com. Accordingly, vitamin C (ascorbic acid) supplementation can typically cause an upset stomach.

Various approaches of administering vitamin C have been described in published literature and various references. Further, numerous approaches of administering vitamins in chewable form have also been described in various references.

For example, Fuisz et al., U.S. Pat. No. 5,965,162, disclose a composition and method for preparing multi-vitamin comestible units which disintegrate quickly in the mouth, especially when chewed. The dosage form is prepared by compressing a formulation containing the medicinal substance and other ingredients which facilitate production and use of the tablet. Vitamin C may be used as the medicinal substance.

Kutilek, III et al., U.S. Pat. No. 5,770,217, disclose a dietary supplement comprising herb extracts, vitamins, minerals and amino acids effective in modulating hematological, immune and appetite enhancement. The vitamin can be vitamin C or another antioxidant.

Gergely et al., U.S. Pat. No. 5,312,626, disclose a chewable tablet comprising an alkali metal and/or earth metal salt and an edible organic acid. This tablet would administer doses of calcium or magnesium in a pleasant fashion.

Stanley et al., U.S. Pat. No. 5,288,497, disclose a composition and method of making a medicament composition that can be absorbed through the mucosal tissues of the mouth, pharynx and esophagus. The medicament can be lipophilic or non-lipophilic. Citric acid is included in the flavoring.

Keane, II, U.S. Pat. No. 5,215,750, discloses compositions comprising a combination of L-glutamine with vitamins, minerals, choline and flavonoids. The composition can be administered to cause weight loss or aid in weight control. The vitamin can be vitamin C, in the form of ascorbic acid.

Bakta et al., U.S. Pat. No. 5,002,780, disclose a dietary supplement comprising vitamin C, as well as vitamin E and magnesium salt of a fatty acid acyl lactylate. The fat soluble nature of this composition allows for excellent absorption of magnesium into the body.

Markham, U.S. Pat. No. 5,070,085, discloses a composition and method for administering therapeutically active compounds which improve the body's absorption of vitamin C. The compositions can also help maintain a healthy level of vitamin C in the body.

Markham, U.S. Pat. No. 4,968,716, discloses compositions and methods for administering therapeutically active compounds, such as antibiotics, analgesics, amino acids and vitamins. The vitamin can be vitamin C. The composition assists in maintaining a healthy vitamin C level in the body.

Borkan et al., U.S. Pat. No. 4,935,243, disclose a chewable, soft gelatin capsule comprising a shell and a biologically active agent, including a drug, a mineral or a vitamin.

Markham, U.S. Pat. No. 4,822,816, discloses a composition for administering vitamin C to a subject. The composition comprises vitamin C with at least one aldono-lactate and edible salt of L-threonic, L-xylonic and L-lyxonic acids.

Puglia et al., U.S. Pat. No. 4,327,077, disclose a compressed soft tablet which disintegrates immediately upon chewing. The tablet may contain an antacid or other active ingredient. The tablet comprises a recrystallized fatty material, a bulking material and a direct compaction vehicle.

Puglia et al., U.S. Pat. No. 4,327,076, disclose a compressed soft tablet which disintegrates immediately upon chewing. The tablet may contain an antacid or other active ingredient. The tablet comprises a recrystallized fatty material, a bulking material and a direct compaction vehicle. The tablet cam be made more palatable with the use of binders, flavors and other tableting aids. Upon chewing this tablet is immediately converted to a smooth, creamy emulsion.

Cavalli et al., U.S. Pat. No. 3,446,899, discloses a vitamin composition containing sorbose, either alone or in combination with a carbohydrate. The sorbose is premixed with an active vitamin ingredient, which can be vitamin C. The tablets may also be chewable.

Elowe et al., U.S. Pat. No. 3,125,491, discloses a chewable vitamin tablet comprising a tablet superimposed onto another tablet to form two layers. One layer consists of a sugar core and the other consists of a vitamin core. The reference discloses that the vitamin may be vitamin C, in the form of ascorbic acid.

Vitamin supplements for pregnant women containing vitamin C and/or folic acid have also been described in various references. Paradissis et al., U.S. Pat. No. 5,869,084, disclose a multi-vitamin and mineral supplement for women comprising a regimen of calcium, vitamin C, vitamin D and vitamin B complex. This supplement is tailored to maximize fetal development and maternal health during each stage of life.

The Physician's Desk Reference describes various vitamin and mineral supplements which contain vitamin C. For example, Natalins® RX, made by Mead Johnson & Company, is a multivitamin and mineral supplement indicated as a dietary pill for use during pregnancy or lactation to be swallowed twice a day. The supplement contains 80 mg of vitamin C and 1 mg of folic acid. See *Physician's Desk Reference*, 1692 ($53^{rd}$ Ed., 1999).

Materna®, made by Lederle Laboratories, is a prenatal vitamin and mineral tablet for use before and during pregnancy and during lactation. The supplement contains 1 mg of vitamin C (as ascorbic acid) and 1 mg of folic acid. See *Physician's Desk Reference*, 1522 ($53^{rd}$ Ed., 1999).

Natafort®, made by Warner Chilcott, is a prenatal multivitamin tablet with iron for use before, during and after pregnancy. The supplement contains 120 mg of vitamin C (as ascorbic acid) and 1 mg of folic acid. See *Physician's Desk Reference*, 3212 ($53^{rd}$ Ed., 1999).

Nestabs® CBF, made by C.B. Fleet Co., is a vitamin and mineral supplement formulated for use during pregnancy and lactation. The supplement contains 120 mg of vitamin C and 1 mg of folic acid. See *Physician's Desk Reference*, 1011 ($53^{rd}$ Ed., 1999).

Niferex® PN, made by Schwarz Pharmaceutical Co., is a vitamin and mineral supplement indicated for the prevention and/or treatment of dietary vitamin and mineral deficiencies associated with pregnancy and lactation. The supplement contains 50 mg of vitamin C (as sodium ascorbate) and 1 mg of folic acid. See *Physician's Desk Reference*, 2916 ($53^{rd}$ Ed., 1999).

Niferex® PN Forte, made by Schwarz Pharmaceutical Co., is a vitamin and mineral supplement indicated for the prevention and/or treatment of dietary vitamin and mineral deficiencies associated with pregnancy and lactation. The supplement contains 80 mg of vitamin C (as ascorbic acid)

and 1 mg of folic acid. See *Physician's Desk Reference*, 2917 (53rd Ed., 1999).

Precare®, marketed by Ther-Rx Corporation, is a prenatal multi-vitamin and mineral supplement for use both by pregnant and lactating women. The supplement contains 50 mg of vitamin C (as ascorbic acid) and 1 mg of folic acid. See *Physician's Desk Reference*, 3163 (53rd Ed., 1999).

Prenate® Ultra Tablets, made by Sanofi Pharmaceuticals, is a multi-vitamin and mineral tablet indicated for use in improving the nutritional status of women throughout pregnancy and in the postnatal period. The supplement contains 120 mg of vitamin C (as ascorbic acid) and 1 mg of folic acid. See *Physician's Desk Reference*, 2802 (53rd Ed., 1999).

Zenate®, made by Solvay Pharmaceuticals, is a multi-vitamin and mineral supplement indicated as a dietary adjunct in nutritional stress associated with periconception, pregnancy and lactation. The supplement contains 70 mg of vitamin C (as ascorbic acid) and 1 mg of folic acid. See *Physician's Desk Reference*, 3128 (53rd Ed., 1999).

While vitamin C plays an essential role as an antioxidant, the acidic nature of current vitamin C supplements, particularly those containing ascorbic acid, generally leads to gastrointestinal problems, such as dyspepsia, gastric upset and diarrhea and teeth problems. In pregnant women vitamin C supplementation is particularly problematic because pregnant women have both an enhanced need for vitamin C and an enhanced susceptibility to dyspepsia and gastrointestinal upset. Further, pregnant women are also very susceptible to nausea, thus making larger vitamin pills difficult to swallow whole. The above described compositions fail to fulfill the need for a chewable prenatal nutritional supplement containing vitamin C without the accompanying side effects, such as gastric upset, dyspepsia, diarrhea, gastric inflammation and tooth enamel erosion, and particularly in individuals with both enhanced vitamin C requirements and enhanced vulnerability to such side effects, such as pregnant women.

Therefore, it would be desirable to provide vitamin C in a chewable form to overcome the difficulties experienced by pregnant women in trying to swallow large pills whole and at the same time provide appropriate amounts of vitamin C in a form designed to minimize or prevent gastric upset, dyspepsia and/or tooth enamel erosion. Accordingly, it would be desirable to provide a nutritional supplement containing vitamin C which overcomes the deficiencies of the currently available vitamin C supplements.

SUMMARY OF THE INVENTION

The present inventive subject matter provides improved vitamin C supplements for pregnant women. The present supplements overcome the deficiencies of current vitamin C prenatal supplements by providing appropriate amounts of vitamin C in a form which is easy for pregnant women to ingest.

One embodiment of the present inventive subject matter is a substantially non-acidic chewable prenatal nutritional composition which comprises: a vitamin C derivative; a folic acid compound present in an amount ranging from about 0.1 mg to about 5.0 mg; and wherein the vitamin C derivative and the folic acid compound are contained together within a stable chewable dosage form having a pH ranging from about 5.5 to about 9.5.

A further embodiment of the present inventive subject matter is a substantially non-acidic chewable prenatal nutritional composition, which comprises: ascorbic acid in an amount ranging from about 25 mg to about 2,000 mg; a non-toxic acid neutralizing alkaline compound in an amount sufficient to substantially neutralize the acidity of the composition; a folic acid compound present in an amount ranging from about 0.1 mg to about 5.0 mg; and wherein the ascorbic acid, the non-toxic acid neutralizing alkaline compound and the folic acid compound are contained together within a stable chewable dosage form.

Another embodiment of the present inventive subject matter is a substantially non-acidic chewable prenatal nutritional composition, which comprises: ascorbic acid or at least one vitamin C derivative; a folic acid compound present in an amount ranging from about 0.1 mg to about 5.0 mg; and wherein the composition is in a stable chewable dosage form having a pH ranging from about 5.5 to about 9.5.

Yet another embodiment of the present inventive subject matter is a substantially non-acidic chewable nutritional composition for males or females planning to conceive a child, which comprises: a vitamin C derivative; a folic acid compound present in an amount ranging from about 0.1 mg to about 5.0 mg; and wherein the vitamin C derivative and the folic acid compound are contained together within a stable chewable dosage form having a pH ranging from about 5.5 to about 9.5.

An even further embodiment of the present inventive subject matter is a substantially non-acidic chewable prenatal nutritional composition, which comprises: a vitamin C derivative; a folic acid compound present in an amount ranging from about 0.1 mg to about 5.0 mg; and wherein the vitamin C derivative and the folic acid compound are contained together within a stable chewable extended release dosage form having a pH ranging from about 5.5 to about 9.5.

The present inventive subject matter also includes a method of administering vitamin C to a pregnant woman without causing gastrointestinal upset, which comprises: administering to the pregnant woman a vitamin C derivative in an amount ranging from about 10 mg to about 1,000 mg; said vitamin C derivative being contained in a stable chewable dosage form; wherein the vitamin C derivative provides vitamin C without causing gastrointestinal upset.

A further embodiment of the present inventive subject matter is a method of administering vitamin C to a pregnant woman without causing gastrointestinal upset or tooth enamel erosion, which comprises: administering to the pregnant woman an amount of ascorbic acid ranging from about 25 mg to about 2,000 mg; a non-toxic acid neutralizing alkaline compound in an amount sufficient to neutralize the acidity of the ascorbic acid; and a folic acid compound in an amount ranging from about 0.1 mg to about 5.0 mg; and wherein the ascorbic acid, the non-toxic acid neutralizing alkaline compound and the folic acid compound are each contained in a stable chewable dosage form.

Another embodiment of the present inventive subject matter is a method of administering vitamin C to a pregnant woman without causing tooth enamel erosion, which comprises: administering to the pregnant woman a vitamin C derivative in an amount ranging from about 10 mg to about 1,000 mg; said vitamin C derivative being contained in a stable chewable dosage form; wherein the vitamin C derivative provides vitamin C without causing tooth enamel erosion.

DETAILED DESCRIPTION OF THE INVENTION

As used herein, "acid neutralizing capacity" is the amount, in milliequivalents (meq), of an alkaline substance that will neutralize a specific amount, in milliequivalents (meq), of acid.

"Active site" refers to a location where an active substance must be present to have its intended effect.

"Biologically active substance" refers to any substance or substances comprising a drug, active therapeutic substance, metabolite, medicament, vitamin, or mineral, any substance used for treatment, prevention, diagnosis, cure or mitigation of disease or illness, any substance which affects anatomical structure or physiological function, or any substance which alters the impact of external influences on an animal, or metabolite thereof, and as used herein, encompasses the terms "active substance", "therapeutic substance", "agent", "active agent", "drug", "medication", "medicine", "medicant", and other such similar terms.

"Chewable dosage form" refers to any forms which are chewed in the mouth after oral administration, or which quickly dissolve after oral administration.

"Form" refers to one discrete unit containing a designated amount of a composition.

"Non-toxic acid neutralizing alkaline compound" refers to any non-toxic compound which when added to a solution containing an acidic compound will increase the pH of the solution.

"Vitamin C derivative" refers to any compound or combination of compounds having vitamin C activity.

"Substantially non-acidic" refers to a range of pH values from about 5.5 to about 9.5; normally, some compositions will exhibit pH values that can be mildly acidic, alkaline or neutral in nature.

The present inventive subject matter provides an improved vitamin C supplement which contains a vitamin C derivative and/or ascorbic acid in combination with a non-toxic acid neutralizing alkaline compound. The present composition provides appropriate levels of vitamin C to pregnant women without accompanying side effects generally associated with vitamin C supplementation, such as gastric upset, dyspepsia and/or tooth enamel erosion. The present composition is superior to previously-available forms of vitamin C in that it is particularly suitable for pregnant women, who are highly susceptible to gastrointestinal problems and nausea. In particular, the nutritional supplement of the present invention is substantially non-acidic (i.e., has a pH range greater than about 5.5) and thus is easier on the stomach and tooth enamel than more acidic vitamin C containing formulations.

Preferably, the composition of the present inventive subject matter has a pH ranging from about 5.5 to about 9.5. More preferably, the composition of the present inventive subject matter has a pH ranging from about 6.5 to about 9.0. Even more preferably, the compositions of the present have a pH ranging from about 7.0 to about 8.5. As discussed herein, the pH of the present composition is measured by any suitable means well known to persons of ordinary skill in the art. For example, without limitation, the pH may be determined by adding 25 ml of deionized water to a container holding the equivalent of 50 mg of ascorbic acid in either the form of ascorbic acid or a salt of ascorbic acid or some combination thereof, stirring vigorously for 10 minutes, and measuring the pH value of the resultant solution/suspension. Another non-limiting exemplary technique for measuring the pH of a dosage form is to use a glass mortar and pestle to grind one tablet until a finely divided uniform powder is obtained. The finely divided uniform powder is then added to an appropriate vessel and the pH is then determined as in manner of the preceding example.

The composition of the present invention may contain a vitamin C derivative. Vitamin C derivatives are any compounds or combinations of compounds having vitamin C activity or antiscorbutic activity, without limitation. Vitamin C derivatives include salts of ascorbic acid, alkaline salts of ascorbic acid, esters of ascorbic acid, oxidation products of ascorbic acid, vitamin C precursors, metabolites of ascorbic acid and its derivatives and combinations thereof. Salts of ascorbic acid, include without limitation, mineral ascorbates and multi-mineral ascorbates. Metabolites of ascorbic acid and its derivatives include, without limitation, aldonic acids, aldono-lactones, aldono-lactides, edible salts of aldonic acids and mixtures thereof. Non-limiting exemplary vitamin C derivatives include calcium ascorbate, magnesium ascorbate, zinc ascorbate, potassium ascorbate, sodium ascorbate, dehydroascorbic acid, L-ascorbic acid 2-0-sulfate, L-ascorbic acid 2-0-phosphate, L-ascorbic acid 3-0-phosphate, L-ascorbic acid 6-hexadecanoate, L-ascorbic acid monostearate, L-ascorbic acid dipalmitate, L-threonic acid, L-xylonic acid, L-lyxonic acid and combinations thereof.

Preferably, the vitamin C derivative is calcium ascorbate, magnesium ascorbate, zinc ascorbate, potassium ascorbate, sodium ascorbate and combinations thereof. More preferably, the vitamin C derivative is calcium ascorbate, magnesium ascorbate, zinc ascorbate, potassium ascorbate and combinations thereof. Even more preferably, the vitamin C derivative is calcium ascorbate.

The present supplements may contain any amount of vitamin C derivative or combinations of vitamin C derivatives. Preferably, the vitamin C derivative is present in the composition in an amount ranging from about 10 mg to about 1,000 mg. More preferably, the vitamin c derivative is present in the composition in an amount ranging from about 20 mg to about 500 mg. Even more preferably the vitamin C derivative is present in the composition in an amount ranging from about 25 mg to about 100 mg.

The present supplements are in a chewable dosage form. The chewable dosage form is advantageous for two reasons. First, pregnant women generally encounter difficulty in swallowing large whole pills, such as the current prenatal nutritional supplements. Secondly, after ingestion of the present supplement the chewing action of the pregnant woman initiates the mixing together of the ascorbic acid and the non-toxic acid neutralizing alkaline compound. This increases the pH of the composition to allow the vitamin C to be administered in a form which is gentler on the gastrointestinal system, as well as the tooth enamel. This is particularly helpful for pregnant women because pregnant women have a reduced tolerance for ingesting acidic substances and swallowing large pills whole. In addition, pregnant women have enhanced need for vitamin C. Therefore, higher levels of vitamin C may be provided through the compositions of the present inventive subject matter without the accompanying increased side effects. Rather the side effects are diminished despite the utilization of larger amounts of vitamin C. This facilitates the use of large doses of vitamin C.

The nutritional supplement is comprised of a stable chewable dosage form. The form may be in any chewable or dissolvable form. Preferably, the dissolvable form will dissolve after oral administration. Non-limiting exemplary forms of the present invention include chewable tablets, quick chew, quick dissolve, particulate matrices, microparticulate matrices, health bars, confections, foods, animal feeds, cereal coatings, cereals, food supplements, nutritional supplements, functional foods, nutritive foods and mixtures thereof. The form comprises either a non-toxic acid neutralizing alkaline compound combined with ascorbic acid or with a vitamin C derivative, or combinations thereof, as well as any necessary additive required to achieve a chewable or quickly dissolvable structure. The ascorbic acid may be physically separated from the non-toxic acid neutralizing alkaline compound so that the compounds do not come into contact with one another until after oral administration, thus conferring stability to the structure.

The ability to obtain chewable or dissolvable forms is performed using well known procedures and techniques available to the ordinary skilled artisan. Each of these specific techniques or procedures for obtaining these structural characteristics do not in themselves constitute an inventive aspect of this invention.

For example, dissolvable tablets, without limitation, may be prepared by combining active components with sugars and cellulose derivatives to form a uniform mixture which is then formed into compressed tablets. The compressed tablets may be formed through direct compression or granulation and then compression, without limitation. The process thus employed can provide a tablet that dissolves or disintegrates after oral administration.

Chewable tablets, without limitation, may be prepared by combining various excipients, such as binders, flavorings, colorants and the like, with active components to form relatively soft, flavored, tablets that can be chewed rather than swallowed whole. Conventional tablet machinery and procedures (both direct compression and granulation) can be utilized. Chewable forms may also be prepared by molding a mixture into a shaped form, immersing the dose forms in a calcium ion bath, recovering the dose forms from the bath, rinsing the dose forms and packaging the dose forms for use. See Vellekoop et al., U.S. Pat. No. 4,765,984. The unit dose forms may be individually wrapped, packaged as multiple units on paper strips or in vials of any size, without limitation. The chewable and dissolvable tablets of the invention may be packaged in unit dose, rolls, bulk bottles, blister packs and combinations thereof, without limitation.

Health bars, without limitation, may be prepared by combining various excipients, such as binders, fillers, flavorings, colorants and the like, along with active components, and mixing to a plastic mass consistency. The mass is then either extruded or molded to form "candy bar" shapes that are then dried or allowed to solidify to form the final product.

Animal feeds, without limitation, may be prepared by combining active components with binding ingredients to form a plastic mass. The mass is then extruded under high pressure to form tubular (or "spaghetti-like") structures that are cut to pellet size and dried.

Cereal or cereal coatings, without limitation, may be prepared by forming the active components into pellets, flakes or other geometric shapes. The pellets, flakes or other geometric shapes are then passed under a precision spray coating device to deposit a film of active ingredients plus excipients onto the surface of the formed elements. The units thus treated are then dried or allowed to dry.

The present compositions may contain ascorbic acid in combination with a non-toxic acid neutralizing alkaline compound. The non-toxic acid neutralizing alkaline compounds for incorporation into the compositions of the present invention include, natural and synthetic alkaline compounds and compounds that react like alkaline compounds, for example, without limitation, calcium-based compounds, antacids, aluminum-based compounds, magnesium-based compounds, sodium-based compounds, potassium-based compounds, proteins, amino acids, fermented products and mixtures thereof. Further non-limiting exemplary non-toxic acid neutralizing alkaline compounds include aluminum carbonate, aluminum hydroxide, aluminum phosphate, aluminum hydroxy carbonate, aluminum citrate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium hydroxide, calcium phosphate, calcium citrate, calcium citrate malate, hydrated magnesium aluminate, activated sulfate, magnesium aluminate, magnesium aluminosilicates, magnesium carbonate, magnesium glycinate, magnesium hydroxide, magnesium oxide, magnesium trisilicate, potassium carbonate, potassium phosphate, potassium citrate, sodium carbonate, sodium bicarbonate, sodium phosphate, sodium citrate and mixtures thereof.

Calcium-based compounds include, but are not limited to, any of the well known calcium supplements, such as calcium carbonate, calcium sulfate, calcium oxide, calcium hydroxide, calcium apatite, calcium citrate-malate, bone meal, oyster shell, calcium gluconate, calcium lactate, calcium phosphate, calcium levulinate, and the like. Derivatives of calcium compounds, as used herein, include, without limitation, salts of calcium, alkaline salts of calcium, esters of calcium, and combinations thereof. The salts and alkaline salts herein refer to those regularly used organic or inorganic salts which are acceptable for pharmaceutical use. The calcium of the present composition may be from any source, without limitation.

The acidity of the ascorbic acid or other acidic components of the present composition may be substantially neutralized by the non-toxic acid neutralizing alkaline compound. The non-toxic acid neutralizing alkaline compound has a total daily dosage of at least the amount required to substantially neutralize the acidity of the composition. The term substantially neutralized refers to the attainment of a pH of at least 5.5. Preferably, the compositions of the present invention contain at least 2 meq of acid neutralizing capacity of the non-toxic acid neutralizing alkaline composition. More preferably, the compositions of the present invention contain at least 5 meq of the non-toxic acid neutralizing alkaline composition. Even more preferably, the compositions of the present invention contain at least 10 meq of the non-toxic acid neutralizing alkaline composition.

The compositions of the present inventive subject matter may optionally contain folic acid, as well as any other vitamins, minerals, nutritional agents, therapeutic agents and the like. In addition to the expected benefits of folic acid, one unexpected benefit arising from the inclusion of folic acid in the present compositions is the increased solubility of folic acid as a result of the pH buffering effect of the composition. In particular, it was unexpectedly discovered that greater absorption of folic acid is achieved when the folic acid is combined with a non-toxic acid neutralizing alkaline compound in a chewable or quickly dissolvable form. This is particularly significant for a pregnant woman because folic acid deficiency in the pregnant woman can result in anemia for the woman and birth defects for the fetus.

Without being limited by theory, one explanation for the unexpectedly increased solubility of the folic acid is that the pre-wetting of the acid neutralizing alkaline compound in the mouth initiates an interaction between the folic acid compound and the non-toxic acid neutralizing alkaline compound which continues as the composition moves through the digestive system. Thus, the chewing or dissolving action in this form, activates the acid neutralizing agent(s) in the mouth, thereby creating an acid neutralizing environment for the folic acid. This interaction continues as the composition moves into the stomach continuing to neutralize the digestive acids of this environment, thereby providing the preferably absorbable form of folic acid to the intestinal tract where it is absorbed into the body. Thus, the interaction between the folic acid and non-toxic acid neutralizing alkaline compound, when administered in a chewable or dissolvable form, facilitates absorption of folic acid because a critical interaction is initiated by the chewing action or dissolving activity in the mouth.

Folic acid or derivatives thereof may be present in the compositions of the present inventive subject matter. Preferably, the folic acid or derivative thereof is present in an amount ranging from about 0.1 mg to about 5 mg. More preferably, the folic acid or derivative thereof is present in the compositions of the present inventive subject matter in an amount ranging from about 0.4 mg to about 3.0 mg. Even more preferably, the folic acid or derivative thereof is present in the compositions of the present inventive subject matter in an amount ranging from about 0.5 mg to about 2.0 mg.

The derivatives of folic acid include compounds formed from folic acid which may be structurally distinct from folic acid, but which retain the active function of folic acid. Non-limiting examples of such derivatives include salts of folic acid, alkaline salts of folic acid, esters of folic acid, chelates of folic acid and combinations thereof.

The present compositions may include any edible mineral or mineral compound. Non-limiting exemplary minerals include calcium, copper, zinc, selenium, magnesium, molybdenum, bioflavonoid, manganese, chromium, iodine, iron, potassium, phosphate and combinations thereof. Non-limiting exemplary mineral compounds include aluminum carbonate, aluminum hydroxide, aluminum phosphate, aluminum hydroxy carbonate, aluminum citrate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium hydroxide, calcium phosphate, calcium citrate, calcium citrate malate, cupric oxide, hydrated magnesium aluminate, activated sulfate, magnesium aluminate, magnesium aluminosilicates, magnesium carbonate, magnesium glycinate, magnesium hydroxide, magnesium oxide, magnesium trisilicate, potassium carbonate, potassium phosphate, potassium citrate, sodium carbonate, sodium bicarbonate, sodium phosphate, sodium citrate, zinc oxide and combinations thereof.

Pharmaceutically acceptable calcium compounds which may be present in the supplements of the present invention include, but are not limited to, any of the well known calcium supplements, such as calcium carbonate, calcium sulfate, calcium oxide, calcium hydroxide, calcium apatite, calcium citrate-malate, bone meal, oyster shell, calcium gluconate, calcium lactate, calcium phosphate, calcium levulinate, and the like.

Preferably, the mineral present is calcium carbonate, calcium citrate, calcium hydroxide, aluminum hydroxide or combinations thereof. More preferably, the mineral present is calcium carbonate. When the mineral is calcium carbonate, preferably the calcium carbonate is present in the composition in an amount ranging from about 20 mg to about 2,000 mg. More preferably, the calcium carbonate is present in the composition in an amount ranging from about 100 mg to about 500 mg. Even more preferably, the calcium carbonate is present in the composition in an amount ranging from about 200 mg to about 400 mg.

The present compositions may also contain an iron compound. Non-limiting exemplary iron compounds include ferrous fumarate, ferrous sulfate, ferric chloride, ferrous gluconate, ferrous lactate, ferrous tartrate, iron-sugar-carboxylate complexes, ferrous succinate, ferrous glutamate, ferrous citrate, ferrous pyrophosphate, ferrous cholinisocitrate, ferrous carbonate, carbonyl iron and mixtures thereof. Preferably, the iron compound is ferrous fumarate, carbonyl iron or mixtures thereof.

The iron compound is preferably present in the composition in an amount ranging from about 10 mg to 200 mg. More preferably, the iron compound is present in an amount ranging from about 20 mg to about 80 mg. Even more preferably, the iron compound is present in the composition in an amount ranging from about 30 mg to about 50 mg.

The present compositions may contain other vitamins in addition to vitamin C. The present compositions may include one or more B vitamins. Preferably, the B vitamin is vitamin B6. More preferably, the B vitamin is pyridoxine.

Preferably, the vitamin B6 is present in the composition in an amount ranging from about 0.1 mg to about 200 mg. More preferably, the vitamin B6 is present in the composition in an amount ranging from about 0.5 mg to 75 mg. Even more preferably, the vitamin B6 is present in the composition in an amount ranging from about 20 mg to about 70 mg.

The present composition may contain vitamin D. Preferably, the vitamin D is present in the composition in an amount ranging from about 100 IU to about 600 IU. More preferably, the vitamin D is present in the composition in an amount ranging from about 200 IU to about 400 IU. Even more preferably, the vitamin D is in the composition in an amount ranging from about 220 IU to about 300 IU.

The present composition may also contain vitamin E. Preferably, the vitamin E is present in the composition in an amount ranging from about 1 IU to about 50 IU. More preferably, the vitamin E is present in the composition in an amount ranging from about 1 IU to about 5 IU. Even more preferably, the vitamin E is present in the composition in an amount ranging from about 2 IU to about 4 IU.

The supplements may include elemental magnesium dosed in the form of one or more pharmaceutically acceptable magnesium compounds, such as magnesium stearate, magnesium carbonate, magnesium oxide, magnesium hydroxide, magnesium sulfate and combinations thereof, without limitation. Preferably, the magnesium compound is magnesium stearate, magnesium oxide and combinations thereof. The magnesium may be present in any appropriate amount. Preferably, the magnesium is present in an amount ranging from about 10 mg to about 500 mg.

Pharmaceutically acceptable copper compounds include cupric oxide, cupric sulfate, cupric gluconate and combinations thereof, without limitation and with cupric oxide being preferred. Preferably, the copper compound is present in the compositions in an amount ranging from about 0.1 mg to about 10 mg.

Useful pharmaceutically acceptable zinc compounds for inclusion in the present compositions include, without limitation, zinc sulfate, zinc chloride, zinc oxide and combinations thereof. Preferably, the comound is zinc oxide. The zinc is preferably present in the compositions in an amount ranging from about 0.5 mg to about 5 mg.

Preferred pharmaceutically acceptable iodine compounds include sodium iodide, potassium iodide and combinations thereof, without limitation, with potassium iodide being most preferred.

The present compositions may contain metabolites of ascorbic acid and its derivatives. Derivatives of metabolites of ascorbic acid include, without limitation, aldonic acids, aldono-lactone compounds, aldono-lactides, edible salts of aldonic acid and combinations thereof. Non-limiting exemplary aldonic acids include L-threonic acid, L-xylonic acid, L-lyxonic acid and combinations thereof. Preferably, the vitamin C of the present compositions is Ester-C®, available from Inter-Cal Corporation, Prescott, Ariz. Ester-C® is described by Markham in U.S. Pat. Nos. 4,822,816; 4,968,716; and 5,070,085.

The composition of the present inventive subject matter may also include one or more biologically active substances or therapeutic substances, including, without limitation, essential fatty acids, hormones, steroids, estrogens, progestins, sedative-hypnotics, barbiturates, benzodiazepines, antidepressants, antinausea agents, tranquilizers, sedatives, osteoporotics, anti-platelets, aminobisphosphonates, herbals, herbal derivatives, plant derivatives, phyto-chemical derivatives and combinations thereof.

Non-limiting exemplary herbals and herbal derivatives include agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, capsicum, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, eucalyptus, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. Johnswort, sarsaparilla, sassafras, saw palmetto, scullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, yucca and combinations thereof. Herbal derivatives, as used herein, refers to herbal extracts, and substances derived from plants and plant parts, such as leaves, flowers and roots, without limitation. Preferably, the herbal or herbal derivative is black cohosh, licorice, false unicorn, siberian ginseng, sarsaparilla, squaw vine, blessed thistle and combinations thereof.

Various additives may be incorporated into the present composition. Optional additives of the present composition include, without limitation, starches, sugars, fats, antioxidants, amino acids, proteins, nucleic acids, electrolytes, derivatives thereof or combinations thereof.

Non-limiting exemplary amino acids of the present inventive subject matter include histidine, isoleucine, leucine, lysine, methionine, phenylalanine, threonine, tryptophan, valine, alanine, arginine, asparagine, aspartic acid, cysteine, glutamic acid, glutamine, glycine, proline, serine, tyrosine, derivatives thereof, and combinations thereof. Preferably, the amino acid present is leucine, isoleucine, valine, derivatives thereof or combinations thereof.

The present invention contemplates the use of pharmaceutically acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Sweetening agents may be selected from a wide range of materials such as water-soluble sweetening agents, water-soluble artificial sweeteners, and dipeptide based sweeteners, including salts thereof and mixtures thereof, without limitation. Preferably, the sweetening agent is glycyrrizin or salts thereof.

Flavors which may optionally be added to the present compositions are those well known in the pharmaceutical art. For example, without limitation, synthetic flavor oils, and/or oils from plants leaves, flowers, fruits and so forth, and combinations thereof are useful. Non-limiting exemplary flavor oils include spearmint oil, peppermint oil, cinnamon oil, and oil of wintergreen (methylsalicylate). Also useful are artificial, natural or synthetic fruit flavors such as citrus oils including lemon, orange, grape, lime, and grapefruit, and fruit essences including apple, strawberry, cherry, pineapple and so forth, without limitation. Preferably, the flavor in the present compositions is vanilla. More preferably, the flavor in the present compositions is french vanilla.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders well known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

The plasticizers used in the dissolution modifying system are preferably previously dissolved in an organic solvent and added in solution form. Preferred plasticizers may be selected from the group consisting of diethyl phthalate, diethyl sebacate, triethyl citrate, cronotic acid, propylene glycol, butyl phthalate, dibutyl sebacate, caster oil and mixtures thereof, without limitation. As is evident, the plasticizers may be hydrophobic as well as hydrophilic in nature. Water-insoluable hydrophobic substances, such as diethyl phthalate, diethyl sebacate and caster oil are used to delay the release of water-soluble vitamins, such as vitamin $B_6$ and vitamin C. In contrast, hydrophilic plasticizers are used when water-insoluble vitamins are employed which aid in dissolving the encapsulated film, making channels in the surface, which aid in nutritional composition release.

The dosage forms of the present invention may involve the administration of a nutritional composition in a single dose during a 24 hour period of time, a double dose during a 24 hour period of time, or more than two doses during a 24 hour period of time, or fractional doses to be taken during a 24 hour period of time. The double or multiple doses may be taken simultaneously or at different times during the 24 hour period.

It is also possible in the nutritional composition of the present invention for the dosage form to combine various forms of release, which include, without limitation, immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is performed using well known procedures and techniques available to the ordinary artisan.

The present composition may be divided into portions and contained in multiple forms or dosage units. When the composition is divided into portions, the portions may be even or uneven portions. One such portion may be administered during the morning or daytime and one may be administered in the evening or nighttime. For example, without being limited thereto, the vitamin C component of the composition could be divided so that one third of the total amount is administered in the morning or daytime and two thirds of the total amount are administered in the evening or nighttime.

The present inventive subject matter also includes methods and nutritional regimens for administering appropriate amounts of vitamin C to a pregnant woman without causing gastric upset, dyspepsia or tooth enamel erosion. The present methods comprise administering either a vitamin C derivative or ascorbic acid in combination with a non-toxic acid neutralizing alkaline compound in a chewable dosage form.

The vitamin C derivative may be any vitamin C derivative that provides vitamin C without causing gastrointestinal upset. A pH buffering agent may be simultaneously administered with the vitamin C derivative or be included directly in the compositions of the present inventive subject matter.

The chewable dosage form may be a prenatal dietary supplement. The prenatal dietary supplement may contain any other vitamins, minerals, nutritional agents and the like, without limitation, as described above.

The chewable dosage forms may any chewable dosage form, as described above. The dosage forms may be provided in any manner. Preferably, the dosage forms are provided to the pregnant woman in a blister pack. More preferably, the dosage forms are provided in a blister pack containing day and/or time indicia to improve patient compliance.

The dosage form may be provided in a manner to facilitate nighttime administration of the vitamin C and/or vitamin B. For example, by using an uneven dosing regimen with larger amounts of the water-soluble vitamins administered at night or the entire amounts administered at night, without limitation.

The present methods may be for any pregnant woman. Certain pregnant women having especially enhanced vitamin C requirements or especially reduced tolerance to ingestion of acidic substances. Such pregnant women include, for example, without limitation, women with low ascorbic acid tolerance, women having a tendency to form kidney stones, women who have high blood pressure or cardiovascular disease, women who are in a high risk pregnancy and women who are immuno-compromised.

The present methods allow above-normal levels of vitamin C to be established and maintained in the body without an accompanying increase in side effects. A pregnant woman's tolerance to vitamin C may also be improved by the present methods.

Although the present compositions and methods are preferably intended for administration to humans, it will be understood that the formulations may also be utilized in veterinary therapies for other animals.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

The following examples are illustrative of preferred embodiments of the invention and are not to be construed as limiting the invention thereto. All percentages are based on the percent by weight of the composition unless otherwise indicated and all totals equal 100% by weight.

EXAMPLE 1

Prenatal Chewable Supplements

The following compositions were used to prepare the prenatal chewable supplements of the present invention:

TABLE I

| COMPONENT | RANGE |
| --- | --- |
| Vitamin C | 10–1000 mg |
| Folic Acid | 0.1–5 mg |
| Calcium Carbonate | 20–2000 mg |
| Iron | 10–200 mg |
| Vitaimn $B_6$ | 0.1–200 mg |
| Vitamin D | 100–600 IU |
| Vitamin E | 1–50 IU |
| Magnesium | 30–150 mg |
| Zinc | 5–100 mg |
| Copper | 0.1–10 mg |

Nutritional supplements incorporating the above formulations were prepared using conventional methods and materials known in the pharmaceutical art in either controlled or immediate release forms. The resulting supplements were recovered and stored for future use. Compositions prepared in accordance with Table I would be substantially non-acidic (e.g., have a pH of at least

EXAMPLE II

Prenatal Chewable Supplement

The following composition was used to prepare the prenatal chewable supplement of the present invention:

TABLE II

| COMPONENT | AMOUNT OF ACTIVE |
| --- | --- |
| Vitamin C (Calcium Ascorbate Ester-C Pharmaceutical Grade 78.9% Vitamin C) | 50 mg |
| Calcium (Calcium Carbonate) | 250 mg |
| Iron (Ferrous Fumarate) | 40 mg |
| Vitamin $D_3$ (Cholecalciferol 500 M IU/g) | 240 IU |
| Vitamin E (di-alpha-Tocopheryl Acetate, SD 500 IU/g) | 3.5 IU |
| Pyridoxine (Pyridoxine HCl, 331/3%, 27.396% Pyridoxine) | 2 mg |
| Folic Acid (Folic Acid, USP 92%) | 1 mg |
| Magnesium (Magnesium Oxide, USP, 60.32% Mg) | 50 mg |
| Zinc (Zinc Oxide, USP, 80.34% Zn) | 15 mg |
| Copper (Cupric Oxide, Powder Ar Grade | 2 mg |

TABLE II-continued

| COMPONENT | AMOUNT OF ACTIVE |
|---|---|
| 79.88% Cu) | |
| Sugar, Compressible | 966 mg |
| Mannitol | 258 mg |
| Lake, Yellow | 12 mg |
| French Vanilla | 50 mg |

Nutritional supplements incorporating the above formulations were prepared using conventional methods and materials known in the pharmaceutical art. The resulting nutritional supplements were recovered and stored for future use. The composition prepared in accordance with Table II would be substantially non-acidic (e.g., have a pH of at least 5.5).

EXAMPLE III

Prenatal Chewable Supplement

The following composition was used to prepare the prenatal chewable supplement of the present invention:

TABLE III

| COMPONENT | AMOUNT OF ACTIVE |
|---|---|
| Vitamin C (Calcium Ascorbate Ester-C Pharmaceutical Grade 78.9% Vitamin C) | 50 mg |
| Calcium (Calcium Carbonate) | 250 mg |
| Iron (Ferrous Fumarate) | 40 mg |
| Vitamin $D_3$ (Cholecalciferol 500 M IU/g) | 240 IU |
| Vitamin E (di-alpha-Tocopheryl Acetate, SD 500 IU/g) | 3.5 IU |
| Pyridoxine (Pyridoxine HCl, 331/3%, 27.396% Pyridoxine) | 2 mg |
| Folic Acid (Folic Acid, USP 92%) | 1 mg |
| Magnesium (Magnesium Oxide, USP, 60.32% Mg) | 50 mg |
| Zinc (Zinc Oxide, USP, 80.34% Zn) | 15 mg |
| Copper (Cupric Oxide, Powder Ar Grade 79.88% Cu) | 2 mg |
| Sugar, Compressible | 966 mg |
| Mannitol | 258 mg |
| Lake, Yellow | 12 mg |
| Flavor, French Vanilla | 50 mg |
| Citric Acid, USP (Anhydrous Powder) | 2 mg |
| Glycyrrizin, Ammoniated | 3.5 mg |
| Flavor, Prosweet Powder (MM55) Natural #875 | 8 mg |
| Stearic Acid | 39 mg |
| Magnesium Stearate | 4.7 mg |

Nutritional supplements incorporating the above formulations were prepared using conventional methods and materials known in the pharmaceutical art. The resulting nutritional supplements were recovered and stored for future use. The composition prepared in accordance with Table III would be substantially non-acidic (e.g., have a pH of at least 5.5).

EXAMPLE IV

Prenatal Chewable Supplement

The following composition was used to prepare the prenatal chewable supplement of the present invention:

TABLE IV

| Component | Dosage Amount |
|---|---|
| Vitamin C | 50 mg |
| Calcium | 250 mg |
| Iron | 40 mg |
| Vitamin $D_3$ | 6 mg |
| Vitamin E | 3.5 mg |
| Pyridoxine | 20 mg |
| Folic Acid | 1 mg |
| Magnesium | 50 mg |
| Zinc | 15 mg |
| Thiamine | 3 mg |
| Riboflavin | 3.4 mg |
| Niacin | 20 mg |
| Vitamin $B_{12}$ | 12 mg |

Nutritional supplements incorporating the above formulations were prepared using conventional methods and materials known in the pharmaceutical art. The resulting nutritional supplements were recovered and stored for future use. The composition prepared in accordance with Table III would be substantially non-acidic (e.g., have a pH of at least 5.5).

EXAMPLE V

The pH Levels of Ascorbic Acid and Calcium Carbonate Mixtures

The pH levels of three ascorbic acid/calcium carbonate compositions falling within the scope of the present inventive subject matter were measured in the following manner: an amount of each composition equivalent to 50 mg (+/−10%) of ascorbic acid was placed in a 150 ml beaker. To the beaker was added 25 ml of deionized water. The contents of the beaker were then vigorously stirred for ten minutes. The pH of the resultant solution/suspension was then measured.

The following table illustrates the results of the above described study:

TABLE V

| Ascorbic Acid | Calcium Carbonate | pH Value |
|---|---|---|
| 50 mg | 500 mg | 7.21 |
| 50 mg | 200 mg | 7.24 |
| 50 mg | 100 mg | 7.17 |
| 50 mg | 0 mg | 3.32 |

Nutritional supplements incorporating the above formulations were prepared using conventional methods and materials known in the pharmaceutical art. As Table V indicates, the compositions were found to be substantially non-acidic (e.g., have a pH of at least 5.5). In fact, all three compositions tested were found to have a neutral pH level.

EXAMPLE VI

The pH Levels of Calcium Ascorbate and Calcium Carbonate Mixtures

The pH levels of three calcium ascorbate/calcium carbonate compositions falling within the scope of the present inventive subject matter were measured in the following manner: an amount of each composition equivalent to 50 mg (+/−10%) of ascorbic acid was placed in a 150 ml beaker. To the beaker was added 25 ml of deionized water. The contents of the beaker were then vigorously stirred for ten minutes. The pH of the resultant solution/suspension was then measured.

The following table illustrates the results of the above described study:

TABLE VI

| Ester-C ®* | Calcium Carbonate | pH Value |
|---|---|---|
| 50 mg | 500 mg | 8.27 |
| 50 mg | 200 mg | 7.99 |
| 50 mg | 100 mg | 8.08 |

*Ester-C ® is a form of vitamin C, available from Inter-Cal Corp., Prescott, Arizona.

Nutritional supplements incorporating the above formulations were prepared using conventional methods and materials known in the pharmaceutical art. As Table VI indicates, the compositions were found to be substantially non-acidic (e.g., have a pH of at least 5.5). In fact, all three compositions tested were found to be slightly above a neutral pH level.

EXAMPLE VII

Comparison of pH Levels of A Conventional Chewable Prenatal Supplement with Chewable Supplements of the Present Invention The pH levels of three calcium ascorbate/calcium carbonate compositions falling within the scope of the present inventive subject matter were measured in the following manner: an amount of each composition equivalent to 50 mg (+/−10%) of ascorbic acid was placed in a 150 ml beaker. To the beaker was added 25 ml of deionized water. The contents were then vigorously stirred for ten minutes. The pH of the resultant solution/suspension was then measured.

The following table illustrates the results of the above described study:

TABLE VII

| Ester-C ®* | Calcium Carbonate | pH Value |
|---|---|---|
| 50 mg | 500 mg | 8.27 |
| 50 mg | 200 mg | 7.99 |
| 50 mg | 100 mg | 8.0 |

*Ester-C ® is a form of vitamin C, available from Inter-Cal Corp., Prescott Arizona.

In comparison, a conventional chewable prenatal supplement containing 1000 IU of vitamin A, 400 IU of vitamin $D_3$, 11 IU of vitamin E, 120 mg of vitamin C, 1 mg of folic acid, 2 mg of vitamin $B_1$, 3 mg of riboflavin, 20 mg of niacin, 10 mg of vitamin $B_6$, 12 mcg of vitamin $B_{12}$ and 29 mg of iron was obtained. The pH value of the above composition was measured in the same manner as above: an amount of each composition equivalent to 50 mg (+/−10%) of ascorbic acid was placed in a 150 ml beaker. To the beaker was added 25 ml of deionized water. The contents were then vigorously stirred for ten minutes or until dissolved. The pH of the resultant solution/suspension was then measured.

The pH values of the above compositions, after performing the study twice, were 4.48 and 4.5. In comparison to the pH levels of the above composition, the pH levels of the calcium carbonate mixtures shown in Table VII were non-acidic, and all values were found to be slightly above the neutral pH level.

EXAMPLE VIII

Comparison of pH Levels of Chewable Prenatal Calcium Ascorbate to pH Levels of Ascorbic Acid/Sodium Ascorbate Compositions The pH level of a chewable prenatal sodium ascorbate composition falling within the scope of the present inventive subject matter was compared to the pH levels of four compositions containing combinations of ascorbic acid and sodium ascorbate. The pH levels were measured in the following manner: an amount of each composition equivalent to 50 mg (+/−10%) of ascorbic acid was placed in a 150 ml beaker. To the beaker was added 25 ml of deionized water. The contents of the beaker were then vigorously stirred for ten minutes. The pH of the resultant solution/suspension was then measured.

TABLE VIII

| Ascorbic Acid | Sodium Ascorbate | pH Value |
|---|---|---|
| 90% | 10% | 3.38 |
| 75% | 25% | 3.72 |
| 50% | 50% | 4.02 |
| 25% | 75% | 4.41 |
| 0% | 100%* | 8.03 |

*calcium ascorbate substituted for sodium ascorbate

Nutritional supplements incorporating the above formulations were prepared using conventional methods and materials known in the pharmaceutical art. As Table VIII illustrates, the prenatal chewable containing only calcium ascorbate has a non-acidic pH of 8.03. In contrast, all four of the ascorbic acid/sodium ascorbate compositions were found to be acidic.

EXAMPLE IX

A chewable composition as set forth herein may be prepared in the following manner. The active nutritional components listed on Table II of Example II above are combined together with the excipients also listed on Table II. The resulting mixture is then blended in a V-shaped blender and feed through the feed hopper of a Stokes BB2 tableting machine. A suitable number of tablets of the desired size may then be compressed.

The invention being thus described, it will be apparent that the same may be varied in many ways. Such variations are not to be regarded as a departure from the spirit and scope of the invention, and all such modifications are intended to be within the scope of the appended claims.

We claim:

1. A substantially non-acidic chewable prenatal nutritional tablet composition, which comprises:
   a vitamin C derivative;
   a folic acid compound present in an amount ranging from about 0.1 mg to about 5.0 mg;
   a flavor, a sweetener, or combinations thereof;
      wherein the vitamin C derivative and the folic acid compound are contained together within a stable chewable dosage form having a pH ranging from about 5.5 to about 9.5; and
      wherein said sweetener is glycyrrizin and pharmaceutical salts thereof.

2. A substantially non-acidic chewable prenatal nutritional tablet composition, which comprises:
   a vitamin C derivative;
   a folic acid compound present in an amount ranging from about 0.1 mg to about 5.0 mg;
   an anti-nausea agent; and
   wherein the vitamin C derivative and the folic acid compound are contained together within a stable chewable dosage form having a pH ranging from about 5.5 to about 9.5.

3. A method of administering vitamin C to a pregnant woman without causing irritation to the esophagus or pharynx or gastrointestinal upset, which comprises:
   administering to a pregnant woman a vitamin C derivative in an amount ranging from about 10 mg to about 1,000 mg; said vitamin C derivative being contained in a stable chewable tablet dosage form having a pH ranging from about 5.5 to about 9.5;
   wherein the vitamin C derivative provides vitamin C without causing gastrointestinal upset.

4. The method of claim 3, further comprising administering a folic acid compound simultaneously with said vitamin C derivative.

5. The method of claim 4, wherein said folic acid is administered in an amount ranging from about 0.1 mg to about 5.0 mg.

6. The method of claim 4, wherein said folic acid is contained together with the vitamin C derivative in said stable chewable tablet dosage form.

7. The method of claim 3, wherein the vitamin C derivative is a mineral ascorbate or a multi-mineral ascorbate.

8. The method of claim 3, wherein the vitamin C derivative is selected from the group consisting of calcium ascorbate, magnesium ascorbate, zinc ascorbate, potassium ascorbate, sodium ascorbate and combinations thereof.

9. The method of claim 3, wherein the vitamin C derivative is administered to the pregnant woman in an amount ranging from about 10 mg to about 1000 mg.

10. The method of claim 3, wherein the vitamin C derivative has a pH ranging from about 6.5 to about 9.0.

11. The method of claim 3, wherein the vitamin C derivative has a pH ranging from about 7.0 to about 8.5.

12. The method of claim 3, wherein the vitamin C derivative is pH neutral.

13. The method of claim 3, wherein the stable chewable tablet dosage form is selected from the group consisting of a chewable tablet, a chewable lozenge, a quick chew, a quick dissolve and combinations thereof.

14. The method of claim 3, further comprising administering a mineral compound to the pregnant woman.

15. The method of claim 3, wherein said mineral compound is selected from the group consisting of calcium carbonate, calcium citrate, calcium hydroxide, aluminum hydroxide, oyster shell calcium and combinations thereof.

16. The method of claim 3, wherein the calcium carbonate is administered to the pregnant woman in an amount ranging from about 20 mg to about 2,000 mg.

17. The method of claim 3, further comprising administering a mineral selected from the group consisting of calcium, magnesium, zinc, copper or combinations thereof to the pregnant woman.

18. The method of claim 3, further comprising administering a pharmaceutically acceptable iron compound to the pregnant woman.

19. The method of claim 18, wherein said pharmaceutically acceptable iron compound is selected from the group consisting of of ferrous fumarate, ferrous sulfate, ferric chloride, ferrous gluconate, ferrous lactate, ferrous tartrate, iron-sugar-carboxylate complexes, ferrous succinate, ferrous glutamate, ferrous citrate, ferrous pyrophosphate, ferrous cholinisocitrate, ferrous carbonate, carbonyl iron and mixtures thereof.

20. The method of claim 18, wherein the pharmaceutically acceptable iron compound is administered in an amount ranging from about 10 mg to 200 mg.

21. The method of claim 3, further comprising administering one or more B vitamins to the pregnant woman.

22. The method of claim 21, wherein the B vitamin is pyridoxine and is administered in an amount ranging from about 0.1 mg to about 50 mg.

23. The method of claim 3, further comprising administering vitamin D in amount ranging from about 100 IU to about 600 IU to the pregnant woman.

24. The method of claim 3, further comprising administering vitamin E in an amount ranging from about 1 IU to about 50 IU to the pregnant woman.

25. The method of claim 3, further comprising administering an aldono-lactone compound to the pregnant woman.

26. The method of claim 3, further comprising administering an edible salt of an aldonic acid to the pregnant woman.

27. The method of claim 26, wherein said aldonic acid is selected from the group consisting of L-threonic acid, L-xylonic acid, L-lyxonic acid and combinations thereof.

28. The method of claim 3, wherein the stable chewable tablet dosage form is a prenatal dietary supplement.

29. The method of claim 3, further comprising administering a pH buffering agent.

30. The method of claim 3, wherein the solubility of folic acid administered simultaneously with the vitamin C derivative is increased in the body of the pregnant woman.

31. The method of claim 3, further comprising administration of a dietary supplement to the pregnant woman.

32. The method of claim 3, further comprising a therapeutic or nutritional regimen for the pregnant woman.

33. The method of claim 3, where in said vitamin C derivative is provided in a blister pack.

34. The method of claim 3, wherein said vitamin C derivative is dosed for nighttime administration.

35. The method of claim 3, wherein the pregnant woman has low ascorbic acid tolerance.

36. The method of claim 3, wherein the pregnant woman has a tendency to form kidney stones.

37. The method of claim wherein the pregnant woman has enhanced vitamin C requirements.

38. The method of claim 3, wherein the pregnant woman has high blood pressure or cardiovascular disease.

39. The method of claim 3, wherein pregnancy presents a high risk for the pregnant woman.

40. The method of claim 3, wherein the pregnant woman is immuno-compromised.

41. The method of claim 3, wherein said method provides vitamin C without causing diarrhea or gastric inflammation.

42. The method of claim 3, wherein normal or above-normal levels of vitamin C are established and maintained in the body of the pregnant woman.

43. The method of claim 3, wherein said method increases the pregnant woman's tolerance to vitamin C.

44. A method of administering vitamin C to a pregnant woman without causing gastrointestinal upset or tooth enamel erosion, which comprises:
   administering to the pregnant woman an amount of ascorbic acid ranging from about 25 mg to about 2,000 mg; a non-toxic acid neutralizing alkaline compound in an amount sufficient to neutralize the acidity of the ascorbic acid; and a folic acid compound in an amount ranging from about 0.1 mg to about 5.0 mg; and
   wherein the ascorbic acid, the non-toxic acid neutralizing alkaline compound and the folic acid compound are each contained in a stable chewable tablet dosage form having a pH ranging from about 5.5 to about 9.5.

45. The method of claim 44, wherein the non-toxic acid neutralizing alkaline compound has a total daily dosage of at least the amount required to substantially neutralize the ascorbic acid present in the stable chewable dosage form.

46. The method of claim 44, wherein the non-toxic acid neutralizing alkaline compound is a mineral compound.

47. The method of claim 46, wherein the mineral compound is selected from the group consisting of aluminum carbonate, aluminum hydroxide, aluminum phosphate, aluminum hydroxy carbonate, aluminum citrate, dihydroxyaluminum sodium carbonate, aluminum magnesium glycinate, dihydroxyaluminum aminoacetate, dihydroxyaluminum aminoacetic acid, bismuth aluminate, bismuth carbonate, bismuth subcarbonate, bismuth subgallate, bismuth subnitrate, calcium carbonate, calcium hydroxide, calcium phosphate, calcium citrate, calcium citrate malate, hydrated magnesium aluminate, activated sulfate, magnesium aluminate, magnesium aluminosilicates, magnesium carbonate, magnesium glycinate, magnesium hydroxide, magnesium oxide, magnesium trisilicate, potassium carbonate, potassium phosphate, potassium citrate, sodium carbonate, sodium bicarbonate, sodium phosphate, sodium citrate, oyster shell calcium and mixtures thereof.

48. The method of claim 44, wherein the non-toxic acid neutralizing alkaline compound is selected from the group consisting of calcium-based compounds, antacids, aluminum-based compounds, magnesium-based compounds, sodium-based compounds, potassium-based compounds and mixtures thereof.

49. The method of claim 44, further comprising a vitamin C derivative.

50. The method of claim 44, wherein the stable chewable tablet dosage form is selected from the group consisting of a chewable tablet, a chewable lozenge, a quick chew, a quick dissolve and combinations thereof.

51. A method of administering vitamin C to a pregnant woman without causing tooth enamel erosion, which comprises:

administering to the pregnant woman a vitamin C derivative in an amount ranging from about 10 mg to about 1,000 mg; and a non-toxic acid neutralizing alkaline compound in an amount sufficient to neutralize the acidity of the vitamin C derivative; said vitamin C derivative being contained in a stable chewable tablet dosage form having a pH ranging from about 5.5 to about 9.5;

wherein the vitamin C derivative provides vitamin C without causing tooth enamel erosion.

* * * * *

UNITED STATES PATENT AND TRADEMARK OFFICE
CERTIFICATE OF CORRECTION

PATENT NO.    : 6,352,713 B1
DATED         : March 5, 2002
INVENTOR(S)   : Mitchell I. Kirschner et al.

It is certified that error appears in the above-identified patent and that said Letters Patent is hereby corrected as shown below:

Column 21,
Lines 5-6, after the phrase "about 1000 mg;" add -- and a non-toxic acid neutralizing alkaline compound in an amount sufficient to neutralize the of the vitamin C derivative; --

Column 22,
Line 36, insert -- 3 -- after "The method of claim"

Signed and Sealed this

Twenty-seventh Day of August, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,352,713 B1 |
| DATED | : March 5, 2002 |
| INVENTOR(S) | : Mitchell I. Kirschner et al. |

It is certified that error appears in the above-identified patent and that said Letters Patent is hereby corrected as shown below:

<u>Column 21,</u>
Lines 5-6, after the phrase "about 1000 mg;" add -- and a non-toxic acid neutralizing alkaline compound in an amount sufficient to neutralize the acidity of the vitamin C derivative; --

<u>Column 22,</u>
Line 36, insert -- 3 -- after "The method of claim"

This certificate supersedes Certificate of Correction issued August 27, 2002.

Signed and Sealed this

Nineteenth Day of November, 2002

*Attest:*

*Attesting Officer*

JAMES E. ROGAN
*Director of the United States Patent and Trademark Office*